(12) United States Patent
Geng et al.

(10) Patent No.: US 12,325,026 B2
(45) Date of Patent: Jun. 10, 2025

(54) INTEGRATED NUCLEIC ACID PROCESSING APPARATUS

(71) Applicant: Delta Electronics, Inc., Taoyuan (TW)

(72) Inventors: Jing Geng, Taoyuan (TW); Yang Liu, Taoyuan (TW); Song-Bin Huang, Taoyuan (TW); Chien-Ting Liu, Taoyuan (TW); Yen-You Chen, Taoyuan (TW); Po-Lin Chou, Taoyuan (TW); Chih-Yang Chen, Taoyuan (TW)

(73) Assignee: Delta Electronics, Inc., Taoyuan (TW)

( * ) Notice: Subject to any disclaimer, the term of this patent is extended or adjusted under 35 U.S.C. 154(b) by 666 days.

(21) Appl. No.: 17/743,229

(22) Filed: May 12, 2022

(65) Prior Publication Data

US 2022/0362780 A1    Nov. 17, 2022

Related U.S. Application Data

(60) Provisional application No. 63/188,746, filed on May 14, 2021.

(30) Foreign Application Priority Data

Apr. 29, 2022   (CN) .......................... 202210468988.9

(51) Int. Cl.
*B01L 7/00* (2006.01)
*A61B 10/00* (2006.01)
(Continued)

(52) U.S. Cl.
CPC ............ *B01L 7/52* (2013.01); *A61B 10/0045* (2013.01); *A61B 10/0096* (2013.01);
(Continued)

(58) Field of Classification Search
CPC ........ B01L 7/52; B01L 3/0227; B01L 3/0234; B01L 3/5029; B01L 2300/021;
(Continued)

(56) References Cited

U.S. PATENT DOCUMENTS 9,850,530 B2    12/2017   Park et al.
2013/0132006 A1*   5/2013   Gwynn .................. B01L 3/021
                                                  702/55
(Continued)

FOREIGN PATENT DOCUMENTS

CN      107022469 A    8/2017
CN      108949505 A    12/2018
(Continued)

*Primary Examiner* — Jennifer Wecker
*Assistant Examiner* — Britney N. Washington
(74) *Attorney, Agent, or Firm* — KIRTON McCONKIE; Evan R. Witt

(57) ABSTRACT

An integrated nucleic acid processing apparatus includes a first operation area, a second operation area and a separation wall. The first operation area includes multiple carrying boards for placing objects and reagents for processing nucleic acids in samples, and multiple operation modules for performing operations of nucleic acid processing. The second operation area includes two extraction regions for respectively performing nucleic acid extractions. The separation wall separates the first operation area from the second operation area and includes two openable door sheets spatially corresponding to the two extraction regions. Nucleic acid extraction plates can be moved from the first operation area to the second operation area by means of the carrying boards as the two openable door sheets are opened, and be isolated in the second operation area for performing nucleic acid extractions as the two openable door sheets are closed.

19 Claims, 15 Drawing Sheets

(51) Int. Cl.
- B01L 3/00 (2006.01)
- B01L 3/02 (2006.01)
- B03C 1/01 (2006.01)
- B03C 1/28 (2006.01)
- G01N 1/02 (2006.01)
- G01N 35/00 (2006.01)
- G01N 35/10 (2006.01)

(52) U.S. Cl.
CPC ........... *B01L 3/0227* (2013.01); *B01L 3/0234* (2013.01); *B01L 3/5029* (2013.01); *B03C 1/01* (2013.01); *B03C 1/288* (2013.01); *G01N 1/02* (2013.01); *G01N 35/1002* (2013.01); *B01L 2300/021* (2013.01); *B01L 2300/0829* (2013.01); *B01L 2300/0832* (2013.01); *B01L 2300/1805* (2013.01); *G01N 2001/028* (2013.01); *G01N 35/0098* (2013.01)

(58) Field of Classification Search
CPC ..... B01L 2300/0829; B01L 2300/0832; B01L 2300/1805; B01L 3/50853; B01L 2300/042; B01L 2300/0609; B01L 2300/0858; A61B 10/0045; A61B 10/0096; B03C 1/01; B03C 1/288; B03C 2201/18; B03C 2201/26; B03C 1/284; B03C 1/286; G01N 1/02; G01N 35/1002; G01N 35/0098; G01N 2001/028; Y02A 50/30; C12M 23/34; C12M 23/06; C12M 23/38; C12M 33/04; B65D 41/04

See application file for complete search history.

(56) References Cited

U.S. PATENT DOCUMENTS

| | | |
|---|---|---|
| 2013/0230860 A1 | 9/2013 | Park et al. |
| 2017/0211058 A1 | 7/2017 | Roth et al. |
| 2017/0269114 A1* | 9/2017 | Bryant ............... G01N 35/0099 |
| 2020/0363299 A1 | 11/2020 | Ye et al. |

FOREIGN PATENT DOCUMENTS

| | | |
|---|---|---|
| CN | 111454839 A | 7/2020 |
| CN | 113088445 A | 7/2021 |
| CN | 113265328 A | 8/2021 |
| CN | 113640535 A | 11/2021 |
| TW | I475230 B | 3/2015 |

* cited by examiner ered Application No. 63/188,746 filed on May 14, 2021 and entitled "AUTOMATIC NUCLEIC ACID PROCESSING WORKSTATION". This application also claims priority to China Patent Application No. 202210468988.9 filed on Apr. 29, 2022. The entireties of the above-mentioned patent application are incorporated herein by reference for all purposes.

FIELD OF THE INVENTION

The present disclosure relates to an integrated nucleic acid processing apparatus, and more particularly to a highly automated integrated nucleic acid processing apparatus.

BACKGROUND OF THE INVENTION

At present, before analyzing nucleic acids in biological samples, multiple processing procedures, e.g., reading barcodes on the sampling tubes, opening and closing the covers of the sampling tubes, transferring samples, extracting nucleic acids, and preparing reagents, are required and involve many operation steps, most of which still have to be done manually. Therefore, the detection efficiency and the detection accuracy are influenced, and the possibility of cross contamination between samples and the risk of operator infection are also increased.

In order to improve the detection efficiency, especially in response to rapid and large detection demands in the event of major public health diseases, there are many automated apparatuses developed for reducing manual work. However, most of these automated apparatuses only integrate parts of the processing procedures but still leave some procedures to be done manually. Especially, the magnetic beads-based nucleic acid extraction which is easy to generate aerosols and cause cross contamination always has to be performed separately. Therefore, the burdens of manual operations still cannot be reduced effectively. In addition, these automated apparatuses generally are bulky and expensive, and thus are not suitable for hospitals in small and medium scales.

Therefore, there is a need of providing an integrated nucleic acid processing apparatus which can effectively reduce the size thereof and also integrate and automatically perform multiple processing procedures so as to reduce the burdens of manual operations.

SUMMARY OF THE INVENTION

An object of the present disclosure is to provide an integrated nucleic acid processing apparatus which integrates processing procedures before the nucleic acid analysis so as to achieve a fully automated operation.

An additional object of the present disclosure is to provide an integrated nucleic acid processing apparatus in which an allocation of the internal space is particularly designed for minimizing the volume.

A further object of the present disclosure is to provide an integrated nucleic acid processing apparatus which can effectively reduce the probability of cross contamination through allocating and partitioning the internal space thereof, such that the automated operation of nucleic acid extraction also can be integrated in the same apparatus.

In accordance with an aspect of the present disclosure, an integrated nucleic acid processing apparatus is provided. The integrated nucleic acid processing apparatus includes a first operation area, a second operation area and a separation wall. The first operation area includes a sampling tube carrying board for placing a plurality of sampling tubes; a pipette tip carrying board for placing at least one tip rack with a plurality of pipette tips accommodated therein; two extraction plate carrying boards, wherein each of the extraction plate carrying boards carries a plurality of nucleic acid extraction plates and each of the nucleic acid extraction plates has a plurality of magnetic rod sleeves disposed therein; a barcode scanner for scanning a plurality of barcodes on the plurality of sampling tubes; a pipettor module for combining with the pipette tips so as to transfer samples in the plurality of sampling tubes to at least one of the plurality of nucleic acid extraction plates; a cover opening and closing module for opening and closing a plurality of covers of the plurality of sampling tubes; and a visual identification module including a camera for capturing an image inside the first operation area. The sampling tube carrying board, the pipette tip carrying board and the two extraction plate carrying boards are respectively mounted on a rail for moving in an X-axis direction. The pipettor module and the visual identification module are moved in a Y-axis direction and a Z-axis direction. The second operation area includes two extraction regions arranged in upper and lower positions. Each of the two extraction regions includes a magnetic rod holder for mounting thereon a plurality of magnetic rods; and a magnetic rod sleeve connector holder for mounting thereon a plurality of magnetic rod sleeve connectors for connecting with the plurality of magnetic rod sleeves disposed in the plurality of nucleic acid extraction plates. The separation wall separates the first operation area from the second operation area and has two door sheets spatially corresponding to the two extraction regions. The two extraction plate carrying boards are spatially corresponding to the two door sheets and arranged in upper and lower positions, the two extraction plate carrying boards are moved from the first operation area to the second operation area as the two door sheets are opened, and a plurality of nucleic acid extraction operations using the plurality of magnetic rods, the plurality of magnetic rod sleeve connectors and the plurality of magnetic rod sleeves are performed and isolated in the second operation area as the two door sheets are closed.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
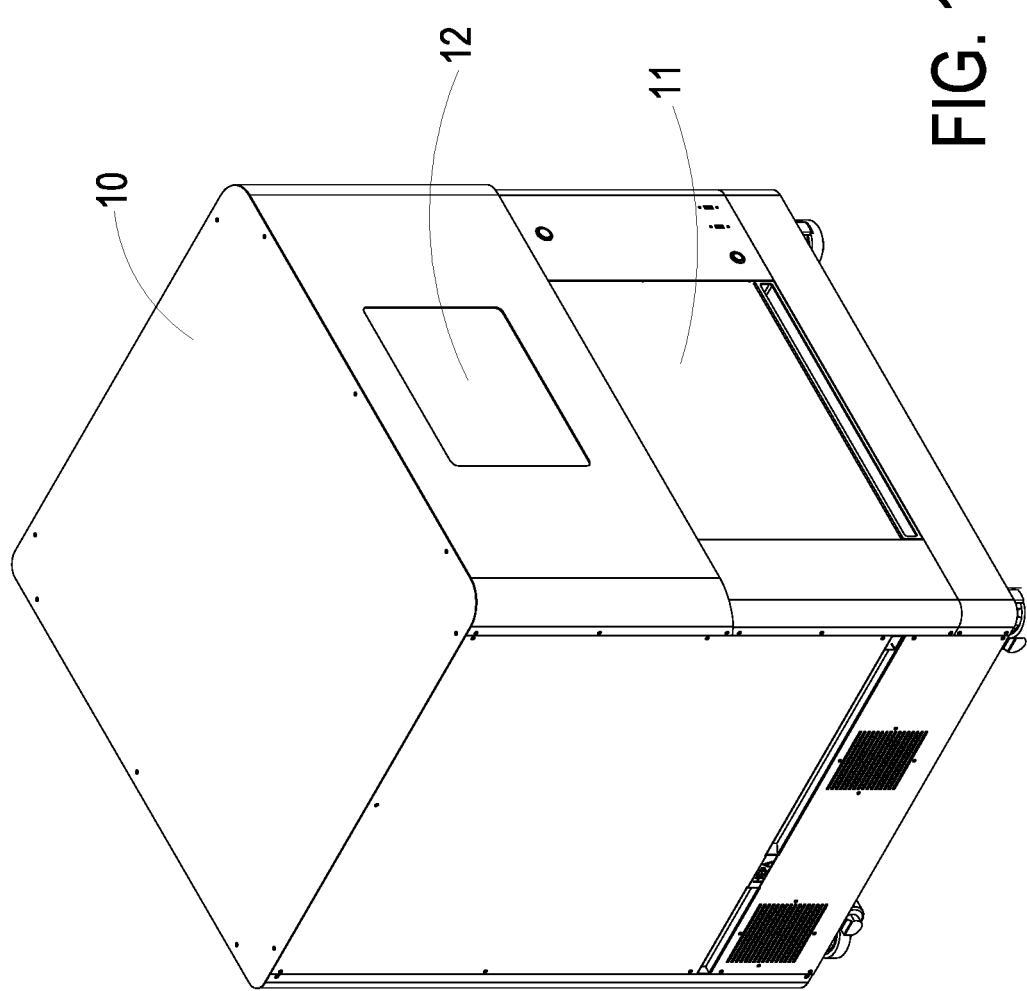
FIG. 1 is a schematic view showing an integrated nucleic acid processing apparatus according to an embodiment of the present disclosure.

Please refer to FIG. 1 which is a schematic view showing an integrated nucleic acid processing apparatus according to an embodiment of the present disclosure. The integrated nucleic acid processing apparatus 1 includes a housing 10 for enclosing an internal space which is independent and isolated from the external environment. The housing 10 includes a door 11 capable of being opened temporarily so as to provide an access entrance for operations in need of entering and exiting the internal space of the integrated nucleic acid processing apparatus 1, e.g., placement and removal of objects. The integrated nucleic acid processing apparatus 1 also includes a controller (not shown) and an operation interface 12 disposed on the housing 10 and electrically connected to the controller. The controller controls various operations of nucleic acid processing in the internal space, and the operation interface 12 is provided for an operator to manipulate the integrated nucleic acid processing apparatus 1. Preferably but not exclusively, the operation interface 12 is a touch screen.

Figure 2A:
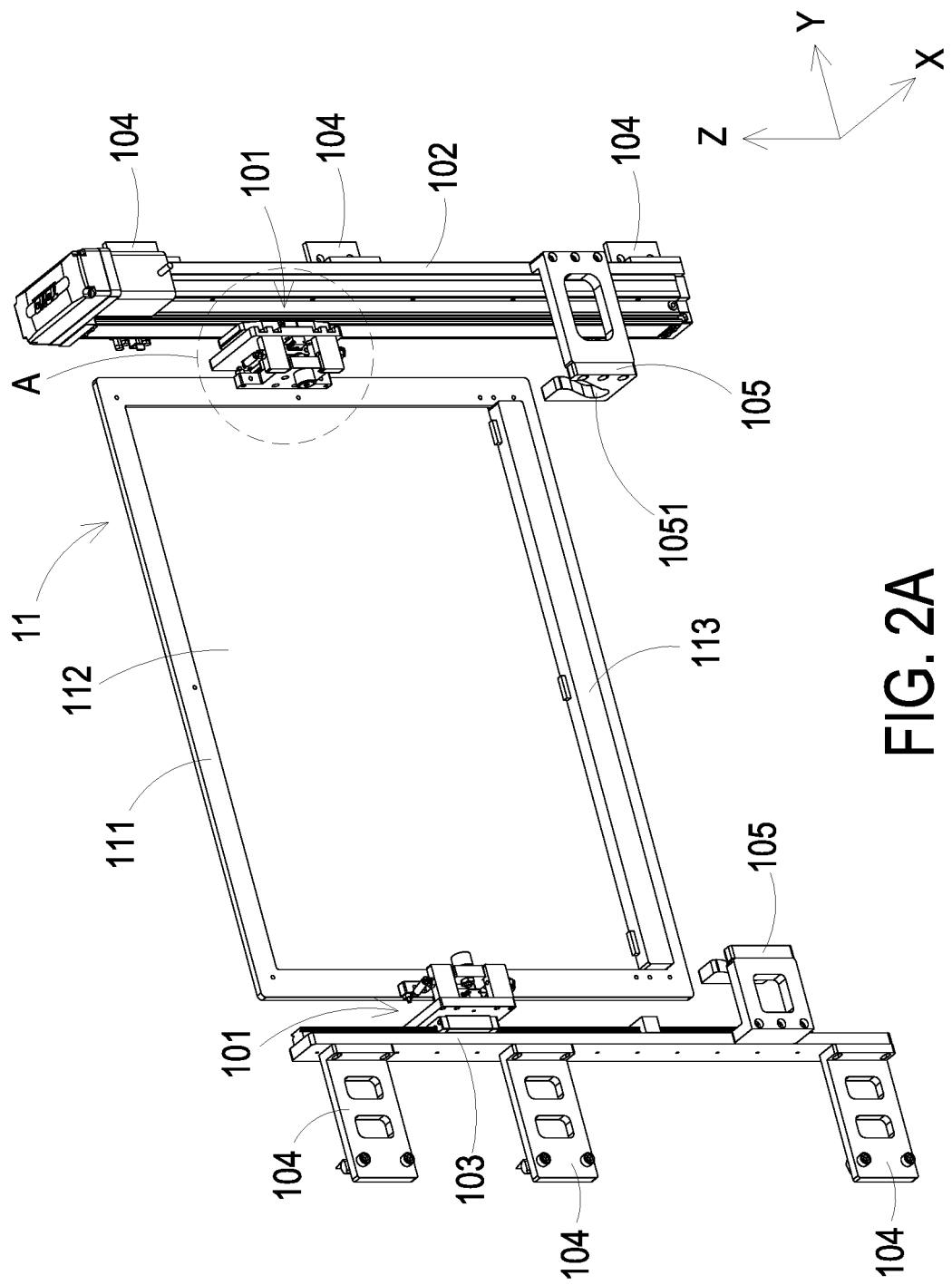
FIG. 2A is a schematic view showing a door and installation components therefor according to an embodiment of the present disclosure.
Figure 2B:
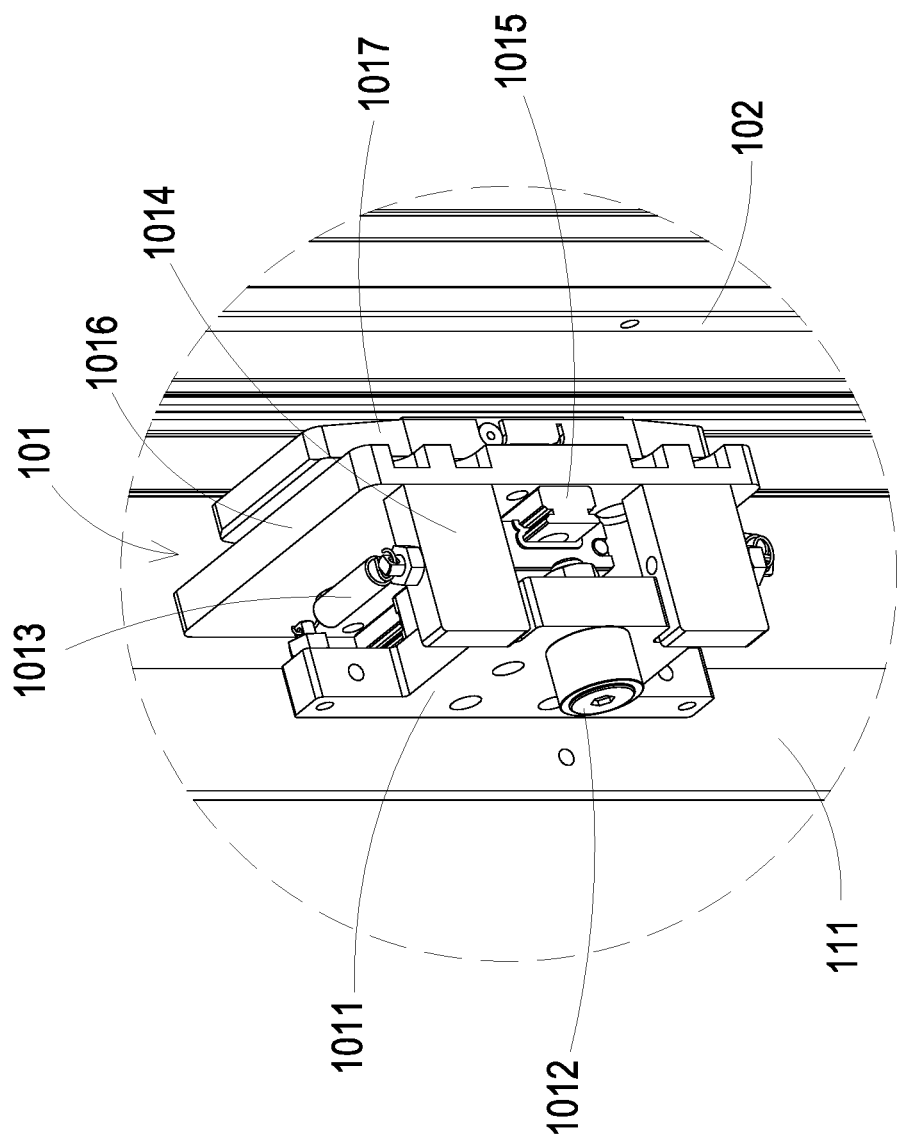
FIG. 2B is an enlarged view of the circle A in FIG. 2A.

Please refer to FIGS. 2A-2B. FIG. 2A is a schematic view showing the door 11 and installation components therefor viewing from interior to exterior of the integrated nucleic acid processing apparatus 1 according to an embodiment of the present disclosure, and FIG. 2B is an enlarged view of the circle A in FIG. 2A. The door 11 includes a door frame 111, a door plate 112 and a handle 113. The door 11 is mounted on a driving side slideway 102 and a driven side slideway 103 through a pair of linear modules 101 so as to be opened up and closed down, namely, to be moved in the Z-axis direction. The driving side slideway 102 and the driven side slideway 103 are mounted on the inner side of the integrated nucleic acid processing apparatus 1 through a plurality of mounting brackets 104. Preferably but not exclusively, the door plate 112 is an acrylic plate.

Each of the linear modules 101 includes a door bracket 1011, a cam 1012, a spring 1013, a spring bracket 1014, a linear guiding rail 1015, a sliding plate 1016 and a sliding block 1017. The sliding blocks 1017 are respectively engaged with the driving side slideway 102 and the driven side slideway 103, and in each of the linear modules 101, the sliding plate 1016 is mounted on the sliding block 1017, the linear guiding rail 1015 is mounted on the sliding plate 1016, and the door bracket 1011 is mounted on the linear guiding rail 1015 and also fixed on the door frame 111 of the door 11, so that when the sliding blocks 1017 are sliding along the driving side slideway 102 and the driven side slideway 103, the door 11 is driven to slide up and down. Further in each of the linear modules 101, the spring bracket 1014 is disposed on the sliding plate 1016, and the longitudinal direction of the spring 1013 is parallel to the linear guiding rail 1015 with one end of the spring 1013 disposed on the spring bracket 1014 and the other end of the spring 1013 disposed on the door bracket 1011. In addition, the linear guiding rail 1015 is substantially perpendicular to the driving side slideway 102 and the driven side slideway 103, that is, the linear guiding rail 1015 provides a forward-and-backward moving direction (i.e., the X-axis direction) for the door bracket 1011 perpendicular to the up-and-down moving direction of the door 11 (i.e., the Z-axis direction). When the door bracket 1011, which is mounted on the sliding plate 1016 through the linear guiding rail 1015, is moved along the linear guiding rail 1015 on the sliding plate 1016, the spring 1013 is stretched to generate a pulling force along the linear guiding rail 1015. For simplifying the description, hereinafter, a moving direction toward the exterior of the apparatus 1 along the X-axis direction is referred to as a forward direction, and a moving direction toward the interior of the apparatus 1 along the X-axis direction is referred to as a backward direction.

The driving side slideway 102 and the driven side slideway 103 further have a guiding plate 105 respectively mounted thereon at a position close to the height of the door 11 when it is closed, and each guiding plate 105 includes a groove 1051 for sliding the cam 1012, which is mounted on the door bracket 1011, therein as the door 11 is moved down. The groove 1051 has a slope gradually away from the interior of the apparatus 1 from up to down, i.e., the groove 1051 slopes forwardly from up to down. Accordingly, during the operation of door closing, when the cam 1012 is slid in the groove 1051, the door bracket 1011 is therefore driven to move forwardly along the linear guiding rail 1015, and thus, the door 11 also has a forward movement along with the downward movement during door closing so as to gradually press toward the housing 10 in contact with the door 11 when it is closed and complete the operation of door closing. Meanwhile, the spring 1013 is under a stretched state, but since the cam 1012 is stuck in the groove 1015, the pulling force of the spring 1013 is restrained and the position of the door 11 is not influenced thereby.

During the operation of door opening, the sliding blocks 1017 of the linear modules 101 drive the sliding plates 1016 and the door 11 to move upwardly, and the cam 1012 is also slid upwardly in the groove 1015. At this time, due to the slope of the groove 1015, the door bracket 1011 is driven to move backwardly and the pulling force of the spring 1013 also acts, and thus the door 11 is moved upwardly and backwardly simultaneously. After the door 11 is moved to a height where the cam 1012 is slid out of the groove 1051, the door 11 is fixed at a rear position, which results in that the door 11 is kept away from other structures inside the apparatus 1 as moving upwardly. Then, as the door 11 is moved to a final height, the operation of door opening is completed.

Figure 3A:
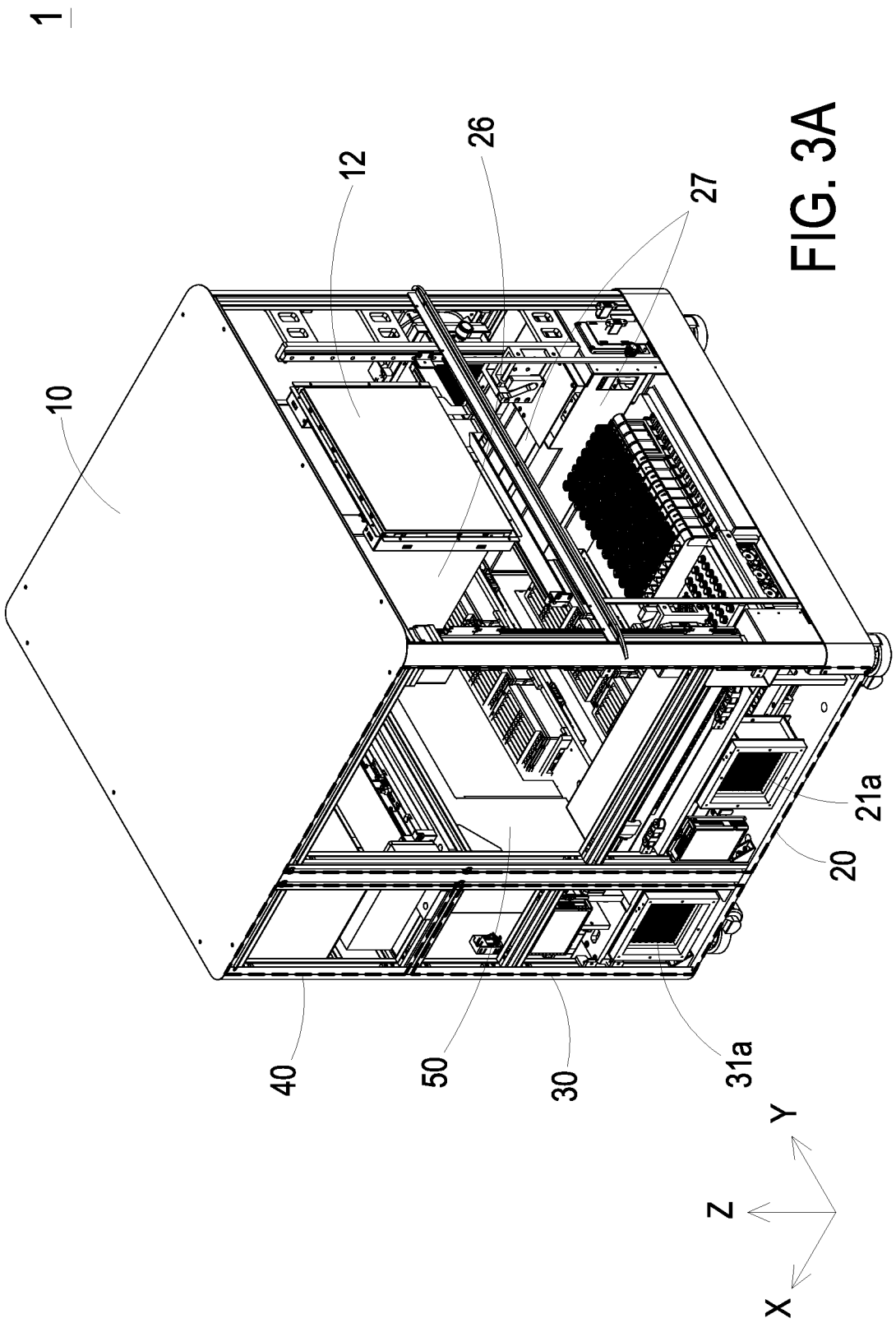
FIG. 3A is a perspective view showing the integrated nucleic acid processing apparatus according to an embodiment of the present disclosure.
Figure 3B:
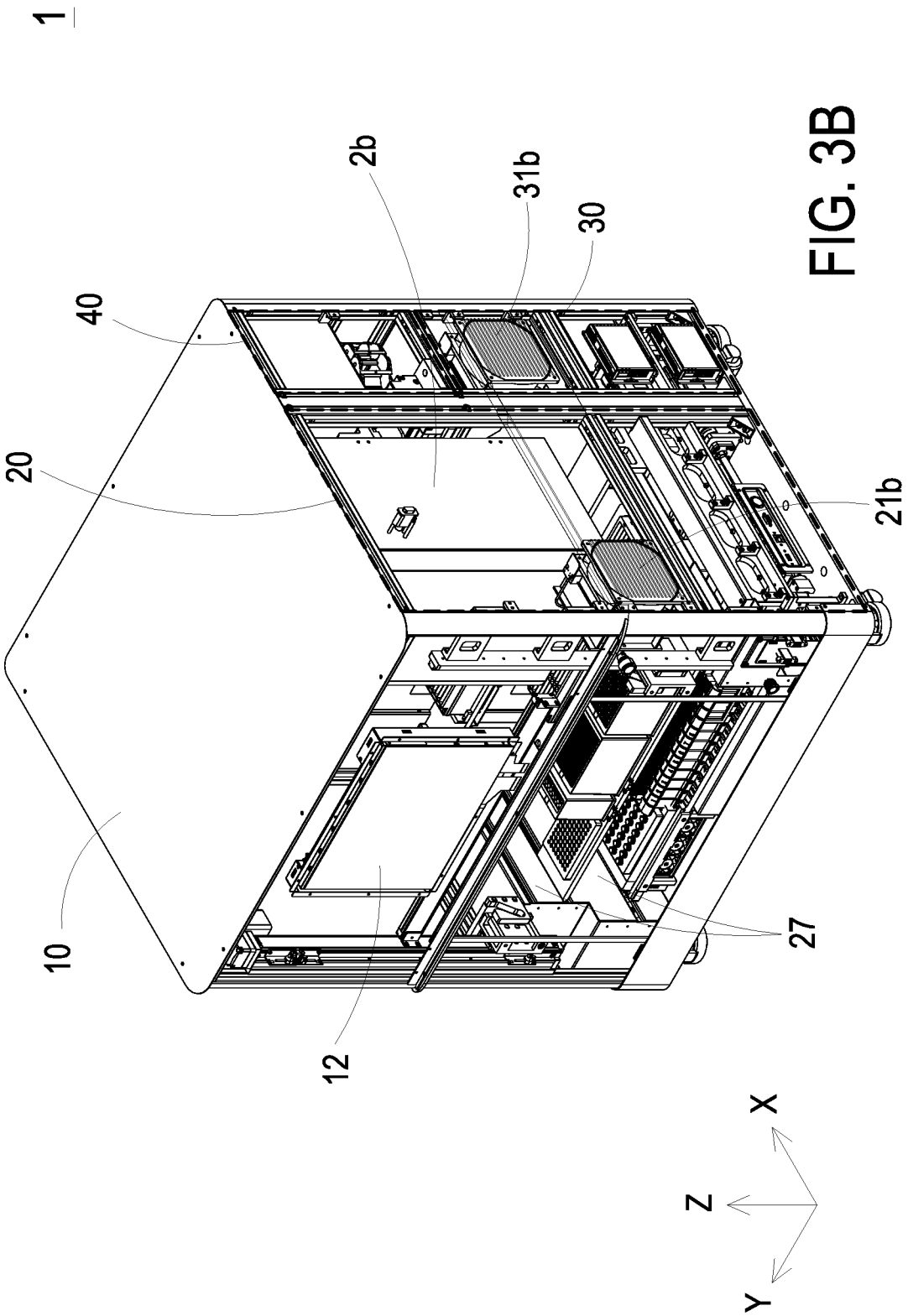
FIG. 3B is a perspective view showing the integrated nucleic acid processing apparatus according to the embodiment of the present disclosure from another view angle.

Please refer to FIGS. 3A-3B. FIG. 3A is a perspective view showing the integrated nucleic acid processing apparatus 1 according to an embodiment of the present disclosure, and FIG. 3B is a perspective view showing the integrated nucleic acid processing apparatus 1 according to the embodiment of the present disclosure from another view angle. The integrated nucleic acid processing apparatus 1 includes a first operation area 20, a second operation area 30 and an electromechanical area 40. The first operation area 20 and the second operation area 30 are main areas for performing operations of nucleic acid processing. The electromechanical area 40 accommodates various electromechanical components required for the operation of the integrated nucleic acid processing apparatus 1, such as controller, motor, power box, integrated circuit board, industrial computer and other related components required for electrical control. The spatial relationship of all areas is the door 11, the first operation area 20 and the second operation area 30 are arranged sequentially in the X-axis direction, namely, the first operation area 20 is closer to the door 11 than the second operation area 30. Further, the electromechanical area 40 is located above the second operation area 30.

The first operation area 20 and the second operation area 30 is separated by a separation wall 50, which results the first operation area 20 and the second operation area 30 respectively to be an independent and isolated space. Thus, the operations of nucleic acid processing performed respectively in the first operation area 20 and the second operation area 30 are separated by the separation wall 50. Accordingly, the possible cross contamination due to the air circulation between two operation areas 20, 30, such as the cross contamination between nucleic acid samples due to aerosols, can be effectively avoided.

The first operation area 20 and the second operation area 30 are respectively designed for different kinds of operations of nucleic acid processing. Within the first operation area 20, the processing procedures, such as barcode scanning, sample transferring and reagent allocation, are performed, and within the second operation area 30, the processing procedures of nucleic acid extraction, such as the magnetic beads-based nucleic acid extraction, are performed. In other words, except the nucleic acid extraction, all other processing procedures required before the nucleic acid analysis are performed in the first operation area 20. During the magnetic beads-based nucleic acid extraction, the violent vibrations of extraction reagents and the movements of magnetic rod sleeves both easily generate aerosols and thus cause cross contamination. Therefore, the isolation of the processing procedures of the nucleic acid extraction in the second operation area 30 greatly contributes to keep the internal space of the apparatus 1 clean.

Accordingly, the first operation area 20 and the second operation area 30 are respectively provided with an independent air circulation system including a first air inlet 21a and a first air outlet 21b disposed at the first operation area 20, and a second air inlet 31a and a second air outlet 31b disposed at the second operation area 30. As shown, the first air inlet 21a and the second air inlet 31a are located at positions lower than those of the first air outlet 21b and the second air outlet 31b. This arrangement results in that the airflow within each operation area is moved in a low-to-high direction, i.e., the air is gradually moved upwardly without a tendency to sink. Thus, even the aerosols are generated, they are also moved upwardly along with the airflow toward the outlets without sinking and causing cross contamination between samples. In an embodiment, high efficiency particulate air (HEPA) filters are disposed at the air inlets 21a, 31a and the air outlets 21b, 31b for ensuring the air flowed in and out of each operation area of the apparatus 1 is filtered to be clean. Moreover, in accordance with different demands, the respective air circulation system of the first operation area 20 and the second operation area 30 can be set to have different operation parameters, such as flow velocity and flow volume. For example, since the nucleic acid extraction which might generate aerosols to cause cross contamination is performed in the second operation area 30, the air circulation system for the second operation area 30 can be set to have a higher flow velocity and a higher flow volume for discharging the aerosols more rapidly. In addition, the first operation area 20 and the second operation area 30 also can have ultraviolet lamps disposed therein for irradiating the interiors thereof so as to achieve the effects of cleaning and sterilization.

In the first operation area 20, an operation module assembly 26, which is used to complete various operations, is hung over the internal space thereof, and multiple carrying boards are located under the operation module assembly 26 for placing all kinds of objects required during operations.

Figure 4:
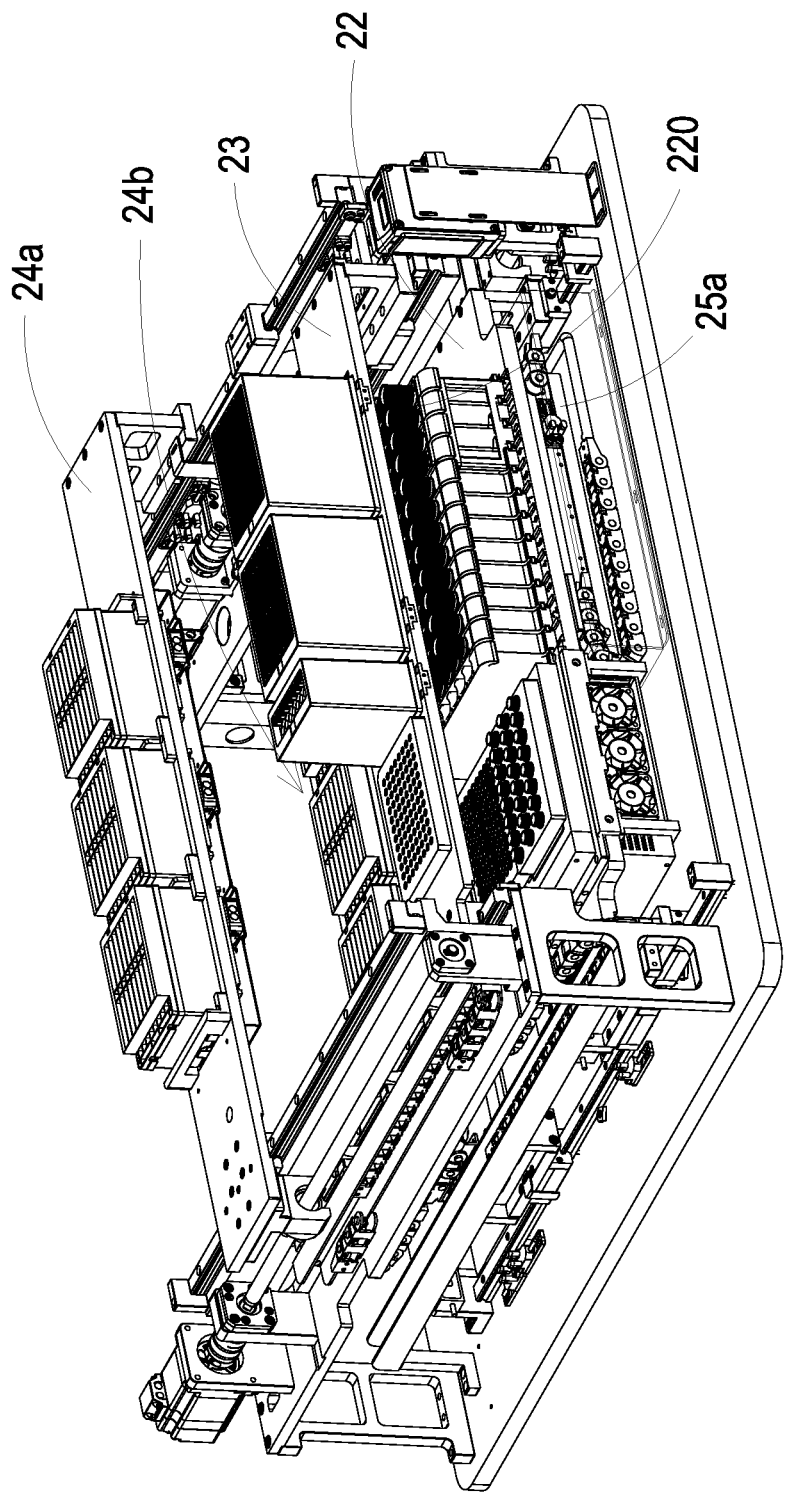
FIG. 4 is a schematic view showing a set of carrying boards in a first operation area according to an embodiment of the present disclosure.

Please refer to FIG. 4 which is a schematic view showing the set of carrying boards in the first operation area 20 according to an embodiment of the present disclosure. For the purpose of automated operation, it is designed to have multiple carrying boards in the first operation area 20 for carrying objects which are classified in accordance with the processing procedures. The set of carrying boards includes a sampling tube carrying board 22, a pipette tip carrying board 23, and two extraction plate carrying boards 24a, 24b. Further, the first operation area 20 also includes a plurality of blocking plates 27 (as shown in FIG. 3A and FIG. 3B) disposed therearound for shielding mechanical structures but leaving space for the carrying boards to move, so as to flatten the space inside the first operation area 20 and reduce blind spots and crevices, thereby avoiding accidental residues of samples from leaving in the crevices which may increase the probability of cross contamination, and also facilitate the cleaning and wiping of the interior of the first operation area 20.

Figure 5A:
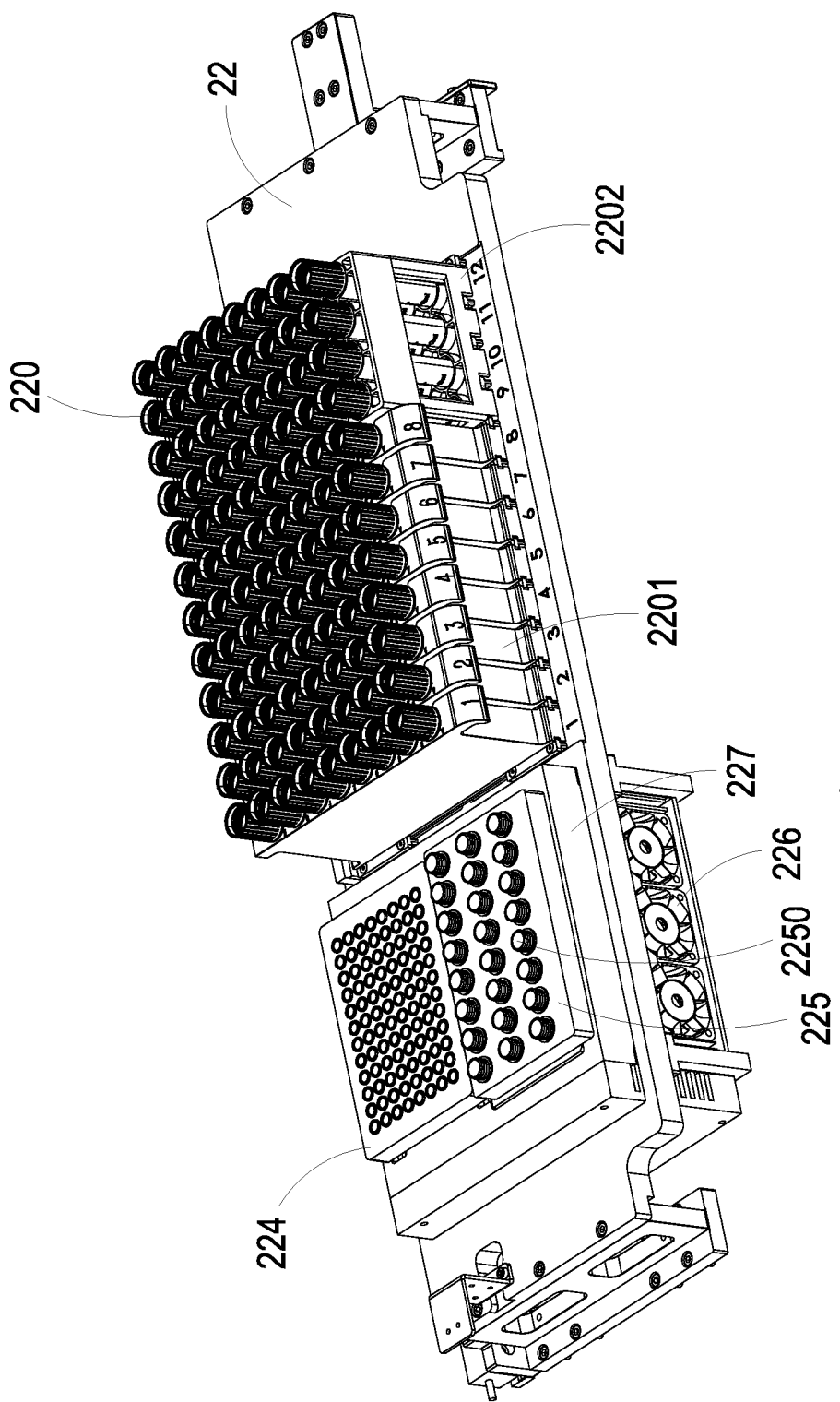
FIG. 5A is a schematic view showing a sampling tube carrying board and configurations thereon according to an embodiment of the present disclosure.
Figure 5B:
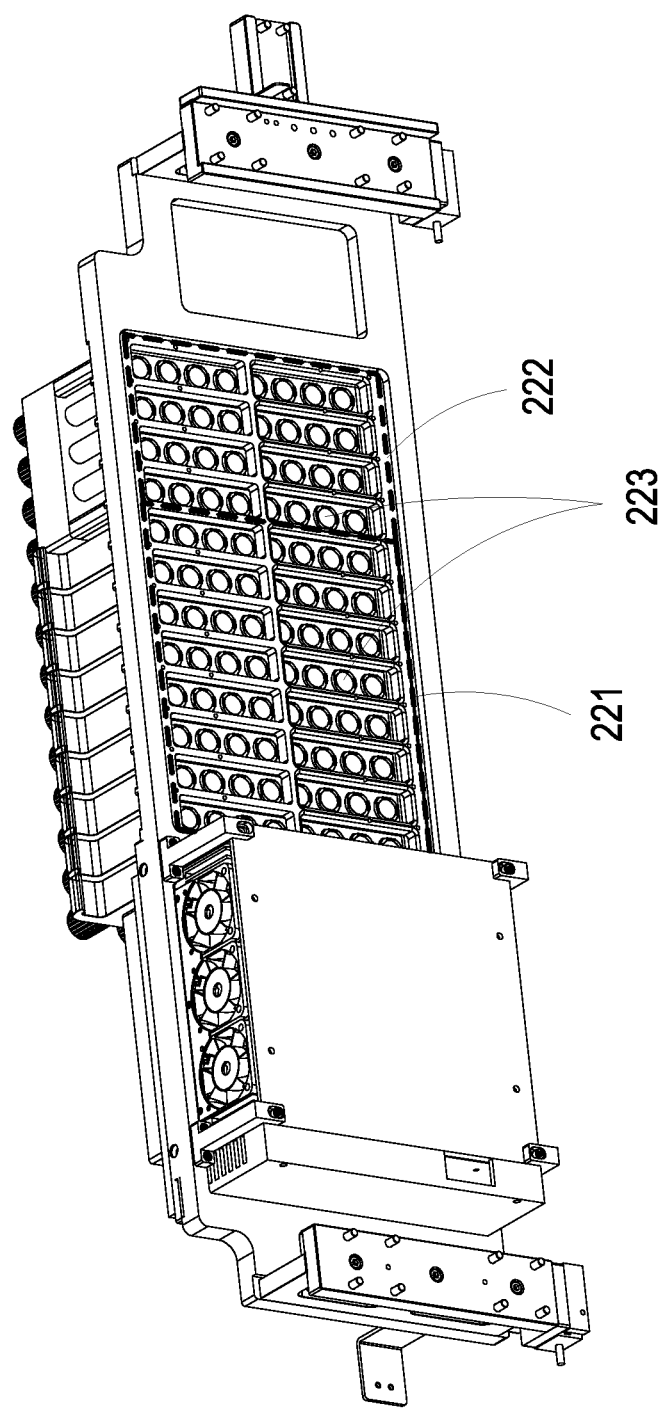
FIG. 5B is a schematic view showing the sampling tube carrying board and configurations thereon according to the embodiment of the present disclosure from another view angle.
Figure 6:
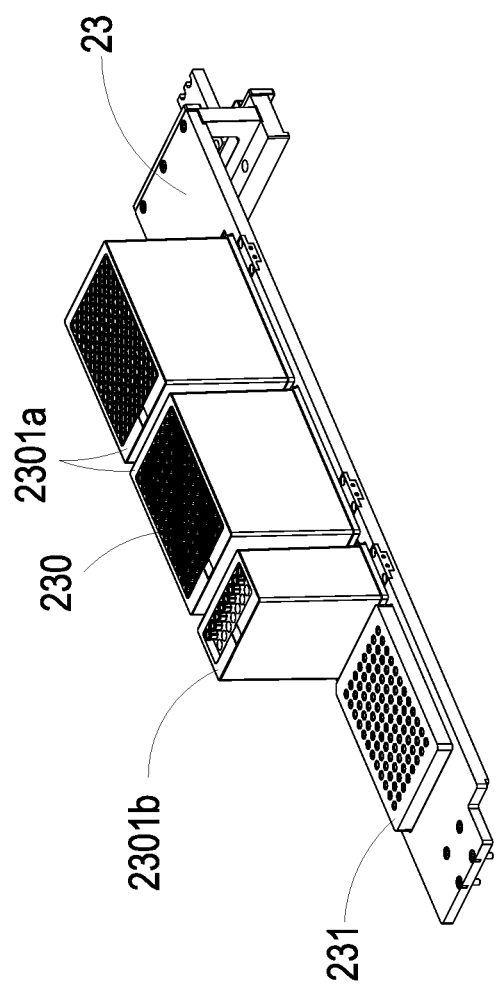
FIG. 6 is a schematic view showing a pipette tip carrying board and configurations thereon according to an embodiment of the present disclosure.
Figure 7A:
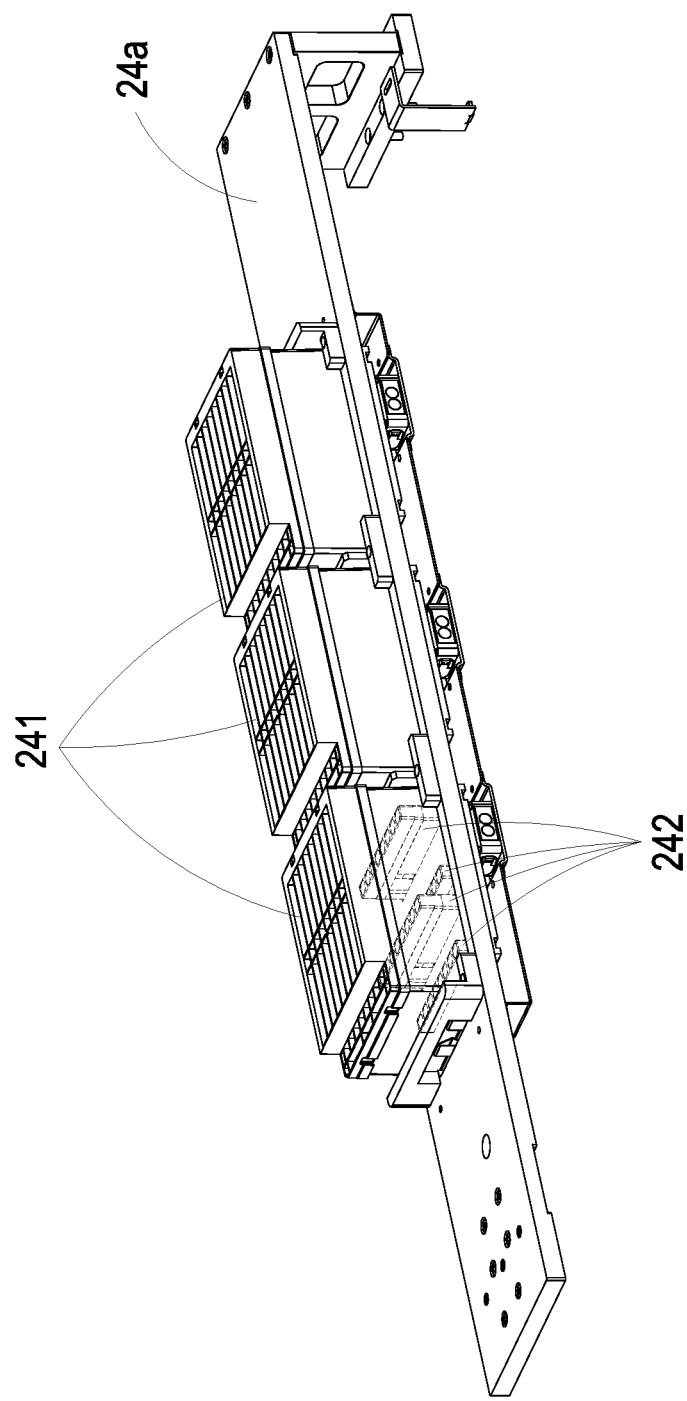
FIGS. 7A-7B are schematic views showing two extraction plate carrying boards and configurations respectively thereon according to an embodiment of the present disclosure.
Figure 7B:
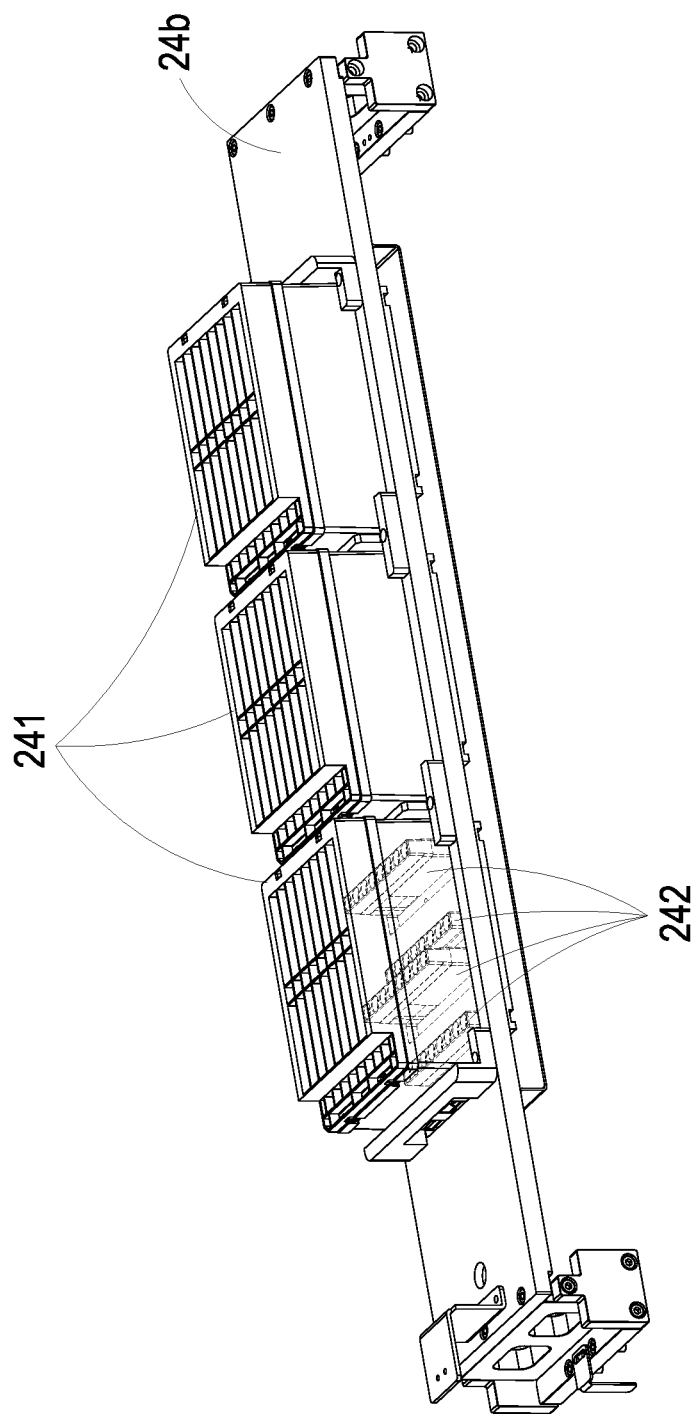

Please further refer to FIG. 4, FIGS. 5A-5B, FIG. 6 and FIGS. 7A-7B. FIG. 5A is a schematic view showing the sampling tube carrying board 22 and configurations thereon according to an embodiment of the present disclosure. FIG. 5B is a schematic view showing the sampling tube carrying board 22 and configurations thereon according to the embodiment of the present disclosure from another view angle. FIG. 6 is a schematic view showing the pipette tip carrying board 23 and configurations thereon according to an embodiment of the present disclosure. FIG. 7A is a schematic view showing the extraction plate carrying board 24a and configurations thereon according to an embodiment of the present disclosure. FIG. 7B is a schematic view showing the extraction plate carrying board 24b and configurations thereon according to an embodiment of the present disclosure. As shown in FIG. 4, the sampling tube carrying board 22, the pipette tip carrying board 23 and two extraction plate carrying boards 24a, 24b are respectively mounted on a corresponding rail and driven by the motor (not shown) to move on the rail in the X-axis direction, namely a direction perpendicular to the door 11. In other words, through the movements on the rails in the X-axis direction, each carrying board can be moved to approach the door 11 for facilitating the operator to place corresponding objects thereon, and after the placement is completed, the carrying board can be moved away from the door 11 and toward the interior of the first operation area 20.

There is a particular spatial arrangement among all carrying boards. The sampling tube carrying board 22 and the extraction plate carrying board 24b are identically located on a first plane, and the sampling tube carrying board 22 is located between the extraction plate carrying board 24b and the door 11, namely, the sampling tube carrying board 22 is closer to the door 11 than the extraction plate carrying board 24b. The pipette tip carrying board 23 is located on a second plane which is higher than the first plane, and the extraction plate carrying board 24a is located on a third plane which is higher than the second plane. In other words, all carrying boards form three moving planes in the first operation area 20, and with the height difference among the moving planes, the pipette tip carrying board 23 and the extraction plate carrying board 24a both can be moved to approach the door 11 for facilitating the operator to place objects. Moreover, when the extraction plate carrying board 24a is moved toward the door 11, it may pass over the pipette tip carrying board 23, and for preventing a collision with the objects on the pipette tip carrying board 23, a sensor (not shown) is additionally disposed on the extraction plate carrying board 24a to sense if there are objects placed on the pipette tip carrying board 23. Furthermore, the sampling tube carrying board 22 and the extraction plate carrying board 24b which are located in the same first plane can be moved together by means of a mechanic connection therebetween, such as a magnetic attraction, so that only single motor is needed to drive the movement of both two carrying boards. In addition, when the extraction plate carrying board 24b is idle, it also can be moved into the second operation area 30 to release the originally occupied space as the moving space for the sampling tube carrying board 22.

The sampling tube carrying board 22 is used to place sampling tubes 220. In response to the existing different types of sampling tubes, the sampling tube carrying board 22 includes a first placing region 221 and a second placing region 222. The first placing region 221 is used to place row-type tube racks 2201 and the second placing region 222 is used to place tray-type tube racks 2202. Through this design, various types of sampling tubes can be used in the present apparatus 1 only if they are placed in the corresponding placing regions. In an embodiment, the first placing region 221 is able to receive eight row-type tube racks 2201 and each row-type tube rack 2201 can receive eight sampling tubes, and in another embodiment, the second placing region 222 is able to receive one 4×8 tray-type tube rack 2202, but not limited thereto. In addition, for the sampling tubes having different diameters, the placements thereof can be achieved by selecting the sizes of the row-type tube rack 2201 and the tray-type tube rack 2202. Therefore, the applicability of the apparatus 1 is improved accordingly.

Furthermore, the first operation area 20 includes barcode scanners disposed therein for scanning barcodes on the sampling tubes 220 carried by the sampling tube carrying board 22. Because the sampling tube carrying board 22 is moved to a position close to the door 11 as placing the sampling tubes, it is preferable to set the barcode scanners close to the door 11. In the embodiment, the first placing region 221 and the second placing region 222 both include a sensor (not shown) for sensing if there is any tube rack placed thereon and identifying where the tube rack is placed, so that the controller accordingly drives the barcode scanners to perform the scanning.

In an embodiment, a bottom barcode scanner 25a is disposed for scanning barcodes at the bottom portions of the sampling tubes 220. In response, the first placing region 221 and the second placing region 222 both have a plurality of hollow outs formed thereon for exposing the barcodes at the bottom portions of the sampling tubes 220. Side walls which constitute each of the hollow outs are also helpful for separating the adjacent barcodes and thus preventing erroneous reading. In another embodiment, a lateral barcode scanner (not shown) also is provided to scan the barcodes at the side walls of the sampling tubes 220. The lateral barcode scanner is mainly employed to scan the sampling tubes in the row-type tube rack 2201 (i.e., the sampling tubes 220 placed in the first placing region 221), so that the sensor at the first placing region 221 is further used to sense the position of the currently placed row-type tube rack 2201 for adjusting the scanning focus of the lateral barcode scanner, that is, the lateral barcode scanner adjusts the focus thereof in accordance with a distance from the row-type tube rack 2201 thereby obtaining clear images of the barcodes.

Moreover, the sampling tube carrying board 22 also carries a nucleic acid assay plate 224 or a plurality of tube strips (not shown) for accommodating the extracted nucleic acids after the nucleic acid extraction. In an embodiment, the nucleic acid assay plate 224 is a 96-well nucleic acid assay plate 224 or may be replaced by twelve 8-tube strips. Further, the sampling tube carrying board 22 additionally carries a reagent tube rack 225 for placing a plurality of reagent tubes 2250, such as 24 reagent tubes, with assay reagents contained therein. In addition, a cooling module 226, such as a cooler, is disposed at a position corresponding to the reagent tube rack 225, so as to maintain the reagents at an appropriate temperature and thus keep the quality and efficacy thereof.

The sampling tube carrying board 22 further has a replaceable adaption board 227 disposed thereon. Depending on different demands, the replaceable adaption board 227 can be replaced to provide flexibility. For example, it can be replaced for placing the nucleic acid assay plate, the plurality of tube strips, and/or the reagent tube rack, or the row-type tube rack or the tray-type tube rack, without limitation.

The pipette tip carrying board 23 carries a plurality of pipette tips 230 which are used for transferring liquids during the operations of nucleic acid processing and are accommodated in tip racks. In an embodiment, the pipette tip carrying board 23 carries two 96-well tip racks 2301a and one 24-well tip rack 2301b for accommodating tips 230 of various volumes, e.g., 1000 µL, 200 µL, 50 µL and/or 10 µL. In the embodiment, each well of the tip rack correspondingly accommodates one tip 230 therein, i.e., each tip 230 is allocated a separate storage space, so that after being used, the tip 230 can be re-positioned in the originally allocated well without contacting the tip in the adjacent well thereby avoiding cross contamination. Further, this also prevents a situation in the prior art that the discarded tips at random angles cause a stacking space thereof higher than the height of the container and thus influence the movement of the carrying board. In the embodiment, the types and amounts of the tip racks and also of the tips can be different based on the practical demands and not limited to the ones illustrated in the figures. Besides, the pipette tip carrying board 23 further carries a collection plate 231, such as a 96-well plate, for multiple usages, for example, for serving as a nucleic acid assay plate or a sample reserving plate, so as to provide selectivity and also increase flexibility of use.

The extraction plate carrying boards 24a, 24b both are used to carry nucleic acid extraction plates 241 for performing nucleic acid extraction. For example, each extraction plate carrying board 24a, 24b can carry three nucleic acid extraction plates 241, and each of the nucleic acid extraction plates 241 includes reagents pre-loaded therein and magnetic rod sleeves (not shown) pre-set therein which are required during the nucleic acid extraction. The extraction plate carrying boards 24a, 24b further include heating modules 242, such as heaters, at the positions corresponding to the nucleic acid extraction plates 241, for providing temperature variations during the nucleic acid extraction, for example, for adjusting the temperature to be 60° C. or 80° C. based on the processing procedures. Notably, each of the extraction plate carrying boards 24a, 24b has the plural heating modules 242 corresponding to the plural nucleic acid extraction plates 241, and for simplification, FIG. 7A and FIG. 7B only perspectively illustrate one heating module 242 corresponding to one nucleic acid extraction plate 241. Furthermore, as shown in FIG. 4, the extraction plate carrying boards 24a, 24b are spatially arranged in upper and lower positions, namely, the third plane where the extraction plate carrying board 24a is located is higher than the first plane where the extraction plate carrying board 24b is located.

Figure 8:
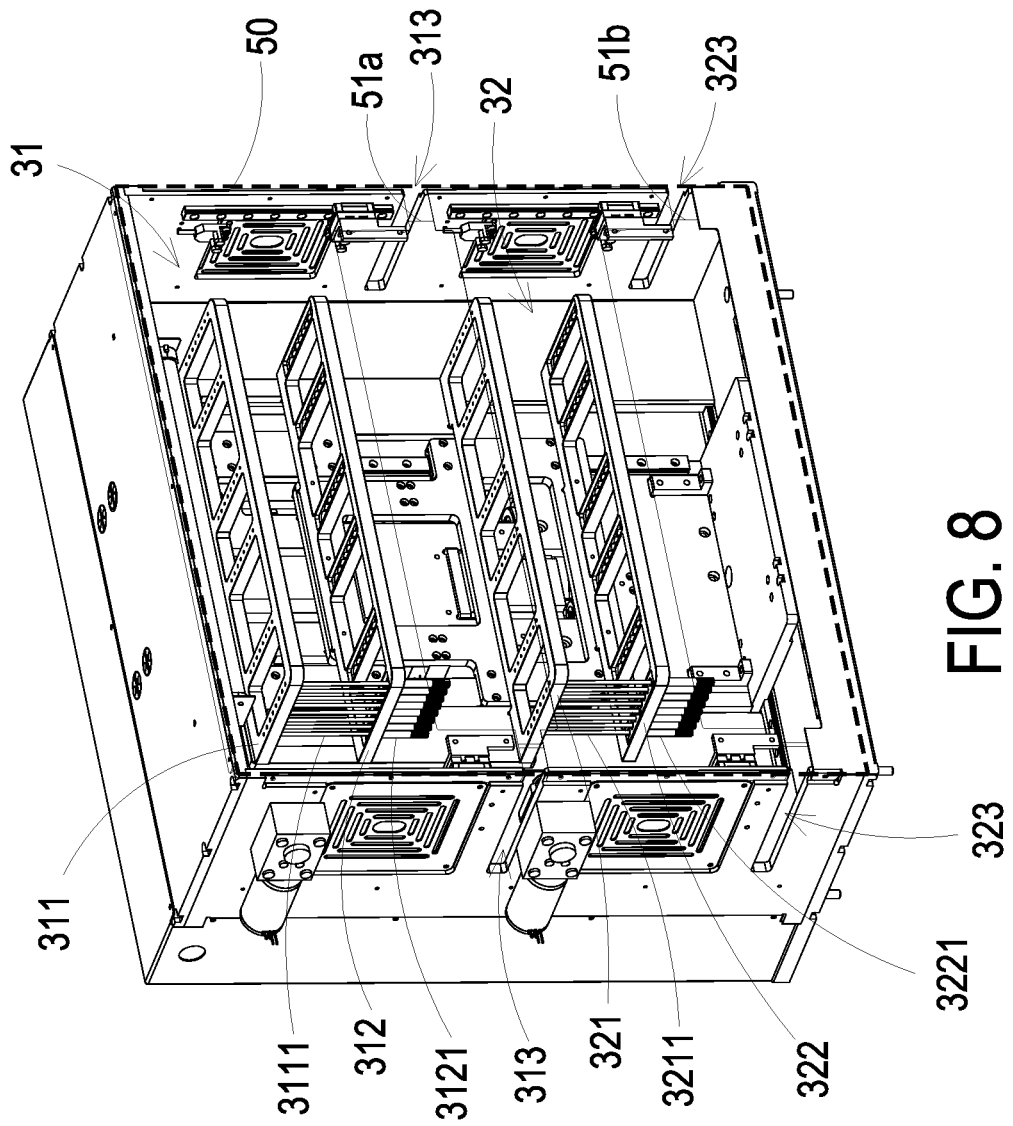
FIG. 8 is a perspective view showing a second operation area according to an embodiment of the present disclosure.

Please refer to FIG. 8 which is a perspective view showing the second operation area 30 according to an embodiment of the present disclosure. The second operation area 30 is divided into two extraction regions 31, 32 which are arranged in upper and lower positions. The separation wall 50, which separates the first operation area 20 and the second operation area 30, includes two door sheets 51a, 51b spatially corresponding to the two extraction regions 31, 32. Further, the positions of the two door sheets 51a, 51b are also spatially corresponding to the respective heights of the extraction plate carrying boards 24a, 24b for passing therethrough the extraction plate carrying boards 24a, 24b and the nucleic acid extraction plates 241 thereon. That is, the extraction plate carrying boards 24a, 24b and the nucleic acid extraction plates 241 thereon can respectively pass through the spaces exposed as the door sheets 51a, 51b are opened for moving into the second operation area 30. In addition, the two extraction regions 31, 32 correspondingly include sliding tracks 313, 323 for the extraction plate carrying boards 24a, 24b to slide into the second operation area 30.

As described above, the second operation area 30 is the space for performing nucleic acid extractions, so the nucleic acid extraction plates 241 loaded with reagents need to be moved into the second operation area 30. In that, since the first operation area 20 and the second operation area 30 are separated by the separation wall 50, the door sheets 51a, 51b are formed to provide temporary passages for the extraction plate carrying boards 24a, 24b to pass as being opened and also isolate the second operation area 30 from the first operation area 20 during performing the nucleic acid extractions as being closed, thereby achieving the automated operation, and at the same time, minimizing the possibility of cross contamination. Preferably but not exclusively, the door sheets 51a, 51b are opened and closed in a straight up and down manner for saving the occupied space. In another preferred embodiment, the door sheets 51a, 51b are opened and closed automatically so as to further smooth the operation procedure. In an embodiment, the automated opening and closing operations of the door sheets 51a, 51b are achieved by a cooperation of motors, linear sliding tracks, synchronous pulleys and synchronous pulley belts, but not limited thereto.

The second operation area 30 includes mechanisms disposed therein for performing the magnetic beads-based nucleic acid extraction, and the configurations of both extraction regions 31, 32 are identical for performing identical magnetic beads-based nucleic acid extractions, so that the number of samples processed at the same time can be increased. The extraction regions 31, 32 respectively include a magnetic rod holder 311, 321 for mounting thereon a plurality of magnetic rods 3111, 3211, and a magnetic rod sleeve connector holder 312, 322 for mounting thereon a plurality of magnetic rod sleeve connectors 3121, 3221 used to connect with the magnetic rod sleeves pre-set in the nucleic acid extraction plates 241. Notably, for simplification, FIG. 8 only illustrates one row of eight magnetic rods 3111, 3211 and one row of eight magnetic rod sleeve connectors 3121, 3221, but the numbers of the magnetic rods and the magnetic rod sleeve connectors are not limited thereto. In an embodiment, the extraction plate carrying boards 24a, 24b respectively carry three nucleic acid extraction plates 241, and each of the nucleic acid extraction plates 241 can be used to process two sets of eight samples, so that each of the magnetic rod holders 311, 321 has correspondingly six rows and total forty-eight magnetic rods 3111, 3211 mounted thereon, and each of the magnetic rod sleeve connector holders 312, 322 also has correspondingly six rows and total forty-eight magnetic rod sleeve connectors 3121, 3221 mounted thereon.

Since the operation procedures of the two extraction regions 31, 32 are the same, the following only takes the extraction region 31 as an example. The nucleic acid extraction can be performed in any one or two of the extraction regions 31, 32 without limitation. The procedures for performing the nucleic acid extraction are as follows. First, the door sheet 51a is opened for passing therethrough the extraction plate carrying board 24a, and then the door sheet 51a is closed. Next, the magnetic rod sleeve connector holder 312 is moved downwardly to connect the magnetic rod sleeve connectors 3121 thereon with the magnetic rod sleeves pre-set in the nucleic acid extraction plates 241. Then, through the up and down movements of the magnetic rod sleeve connector holder 312, the magnetic rod sleeves connected with the magnetic rod sleeve connectors 3121 are simultaneously moved to sequentially perform the steps of magnetic beads-based nucleic acid extraction in each well of the nucleic acid extraction plates 241, e.g., the steps of cell lysis, nucleic acid adsorption, washing and elution. During these processes, when there is a need to absorb the magnetic beads, the magnetic rod holder 311 is moved downwardly to make the magnetic rods 3111 mounted thereon to pass through the magnetic rod sleeve connectors 3121 and arrive the bottom portions of the magnetic rod sleeves, so that the magnetic beads in the wells of the nucleic acid extraction plates 241 are absorbed by the magnetic rods 3111, and the magnetic rod holder 311 and the magnetic rod sleeve connector holder 312 are moved together to transfer the absorbed magnetic beads to the next wells. Then, the magnetic rod holder 311 is moved upwardly to separate the magnetic rods 3111 from the magnetic beads and thus release the magnetic beads, and at the same time, the magnetic rod sleeves are driven by the magnetic rod sleeve connector holder 312 to have up-and-down vibrations for speeding up the dispersion of magnetic beads to be mixed with the liquid.

As performing the magnetic beads-based nucleic acid extraction, the magnetic rod sleeves need to move upwardly and downwardly in the wells and to move among wells sequentially, namely, to move in the Y-axis direction and the Z-axis direction, so that it is important the movements of the magnetic rod sleeves and the magnetic rods are along straight lines and not deviated. In that, the magnetic rod holder 311 and the magnetic rod sleeve connector holder 312 respectively have a linear lead screw set (not shown) disposed thereon for ensuring the movements in the Z-axis direction and in the Y-axis direction both are correct without offset. Further, because the magnetic rod holder 311 and the magnetic rod sleeve connector holder 312 also need to move together, linear sliding tracks are further provided along with roller clamping so as to ensure a synchronous movement between the two without misalignment.

Figure 9A:
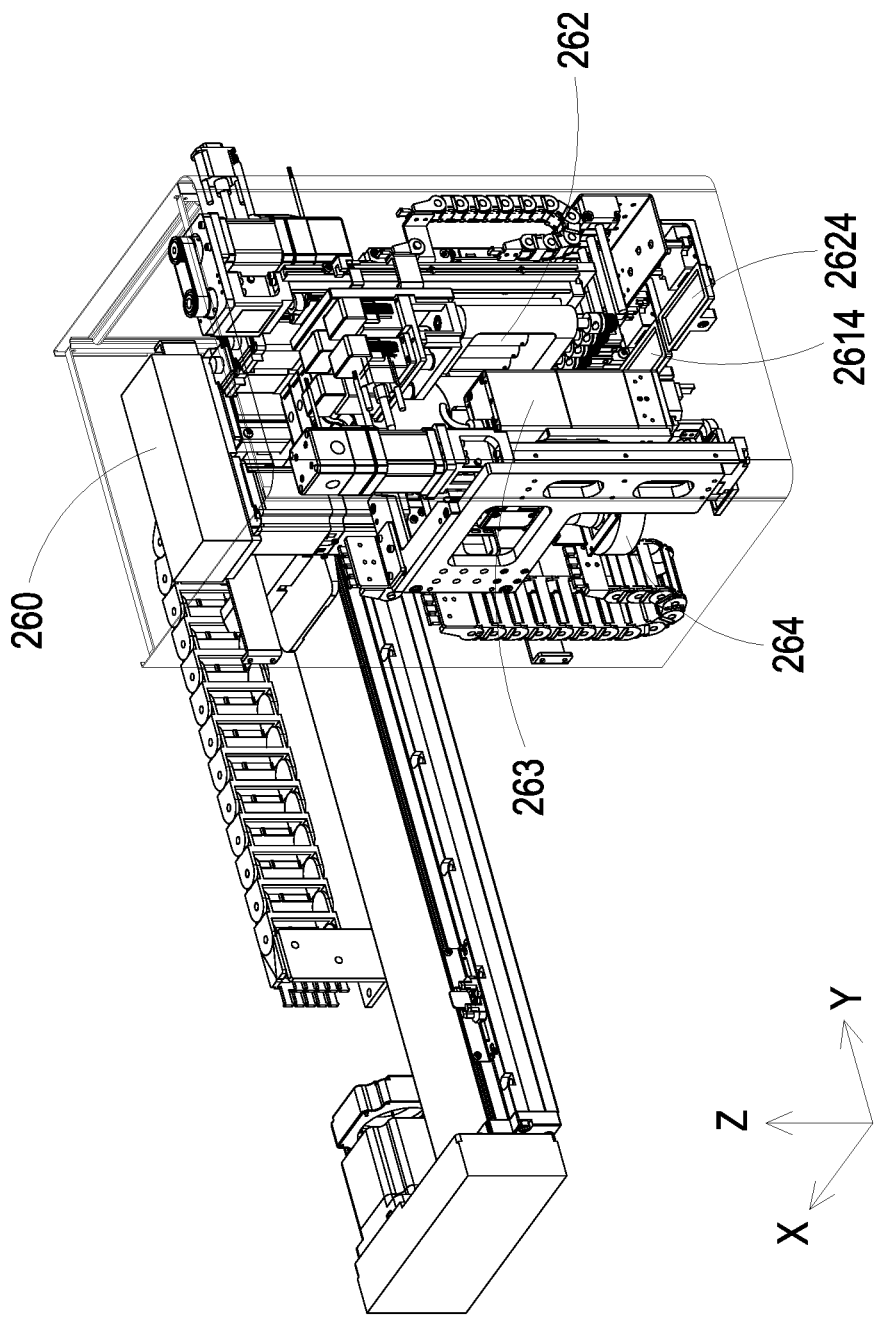
FIG. 9A is a perspective view showing an operation module assembly according to an embodiment of the present disclosure.
Figure 9B:
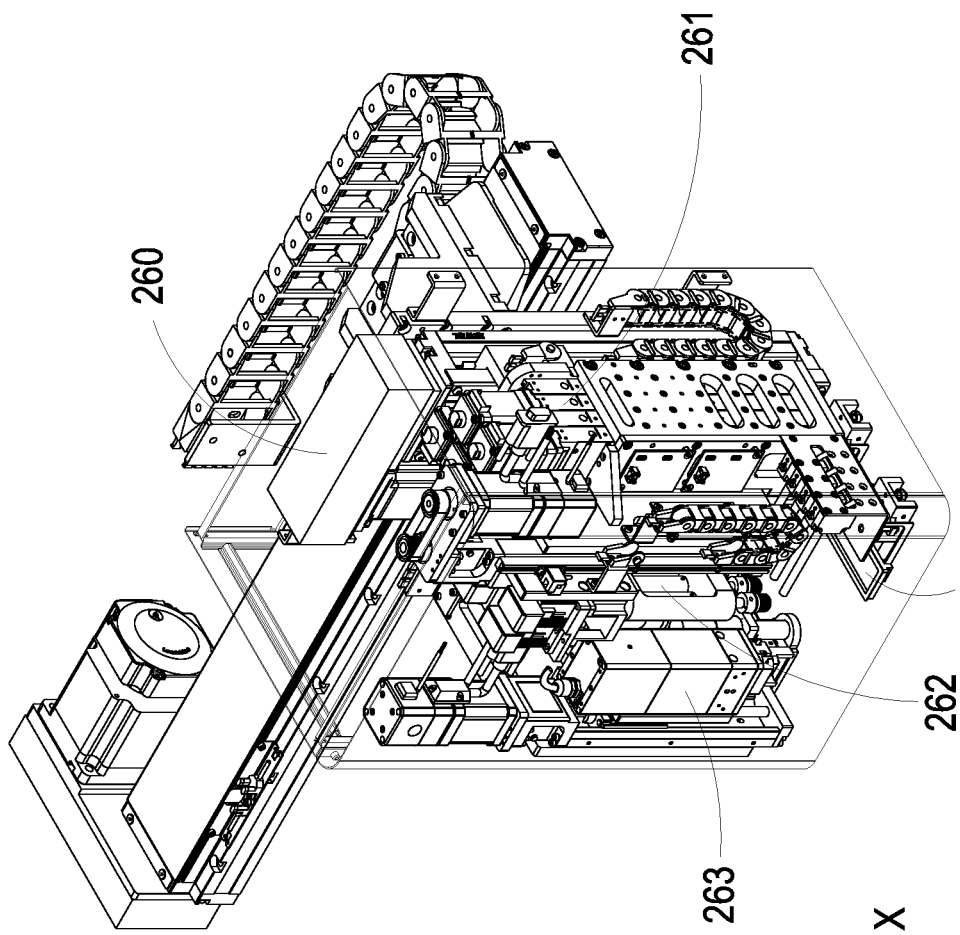
FIG. 9B is a perspective view showing the operation module assembly according to the embodiment of the present disclosure from another view angle.
Figure 10:
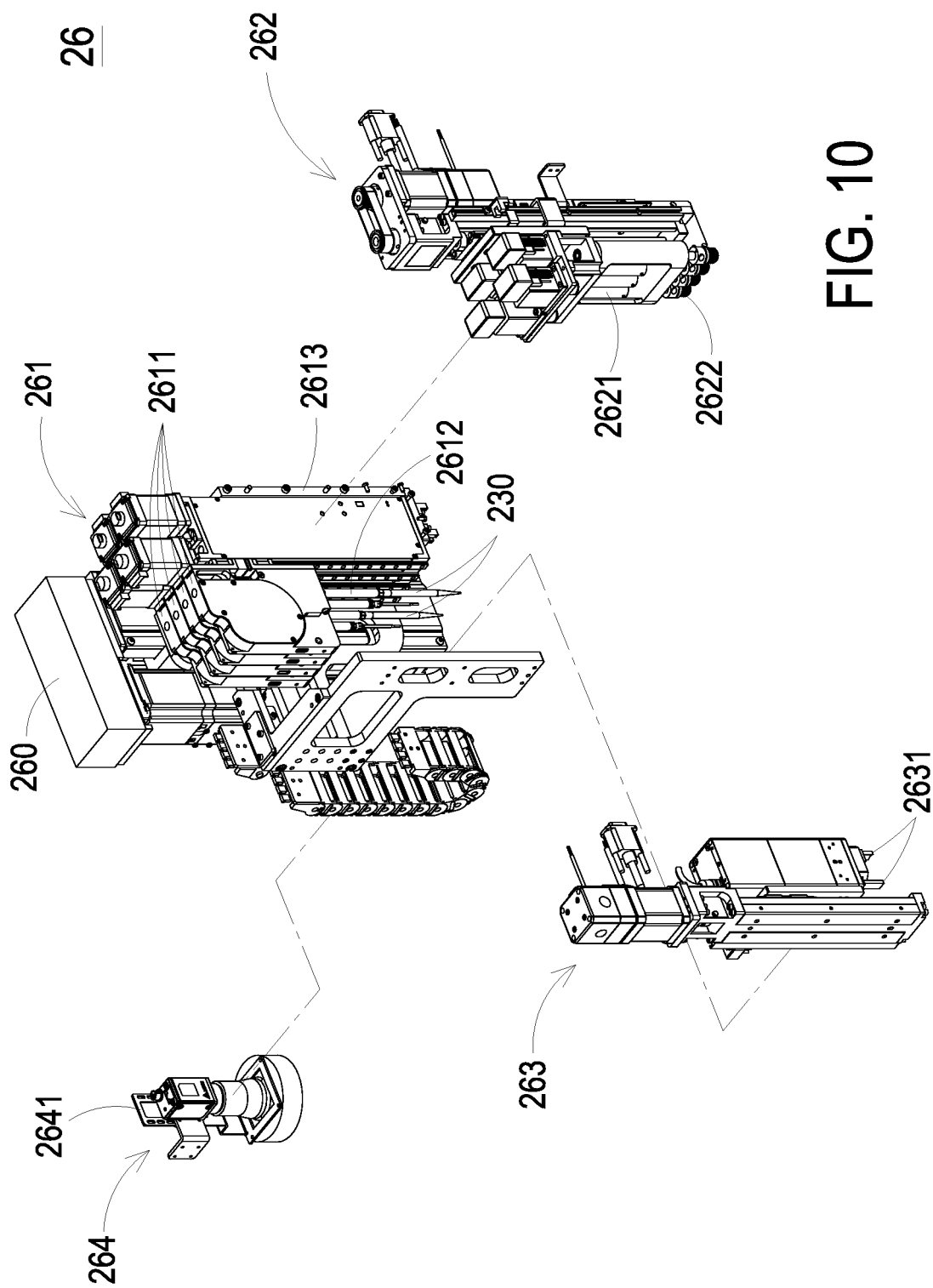
FIG. 10 is an exploded schematic view showing the operation module assembly according to the embodiment of the present disclosure.

Please refer to FIGS. 9A-9B and 10. FIG. 9A is a perspective view showing the operation module assembly 26 according to an embodiment of the present disclosure, FIG. 9B is a perspective view showing the operation module assembly 26 according to the embodiment of the present disclosure from another view angle, wherein the view angles of FIGS. 9A-9B are identical to those of FIGS. 3A-3B, and FIG. 10 is an exploded schematic view showing the operation module assembly 26 according to the embodiment of the present disclosure. The operation module assembly 26 is designed to have a movement direction perpendicular to that of the carrying boards, i.e., to have a movement direction in the Y-axis direction. In other words, the carrying boards 22, 23, 24a, 24b are located at the lower space of the first operation area 20 and moved in the X-axis direction, and the operation module assembly 26 is located at the upper space of the first operation area 20 and moved in the Y-axis direction.

The operation module assembly 26 includes a base 260, a pipettor module 261, a screwing-type cover opening and closing module 262, a clamping-type cover opening and closing module 263, and a visual identification module 264. The base 260 is connected with each module for providing each module with the power to move in the Z-axis direction and to individually execute the operation, and thus, each module is capable of moving in the Y-axis direction and the Z-axis direction. Further, each module is engaged with the base 260 through an independent fixing plate, so that each module can be disassembled independently for maintenance.

The pipettor module 261 is used to combine with the pipette tips 230 (as shown in FIG. 6) for transferring and mixing liquids, for example, for transferring the liquids in the sampling tubes 220 to the nucleic acid extraction plates 241, or transferring the extracted nucleic acids to the nucleic acid assay plate 224 or the collection plate 231. The pipettor module 261 includes at least one pipettor set 2611, a pipettor fixing plate 2613 for fixing with the base 260, and at least one tray 2614 for receiving liquids that might drip from the pipette tips 230 during moving. Further, the pipettor set 2611 includes a pipettor 2612 for automatically grabbing the pipette tip 230 and automatically ejecting the pipette tip 230 after use. In an embodiment, the pipettor module 261 includes four pipettor sets 2611, and each pipettor set 2611 independently moves in the Z-axis direction.

The screwing-type cover opening and closing module 262 and the clamping-type cover opening and closing module 263 are respectively responsible for different kinds of cover opening and closing operations, and employing two kinds of cover opening and closing modules is advantageous that the apparatus 1 can universally receive different types of sampling tubes without limitation. The screwing-type cover opening and closing module 262 is aimed at the kind of sampling tube with a cover having thread structures at two opposite sides. In an embodiment, the screwing-type cover opening and closing module 262 includes a plurality of columns 2621 and the front end of each column 2621 has threads 2622. Each column 2621 can be moved in the Z-axis direction independently and the threads 2622 thereof can be screwed with the threads at one side of the cover of the sampling tube. Namely, the threads at said side of the cover are matched with the threads 2622, so that the two can be screwed to engage or disengage. Further, the screwing-type cover opening and closing module 262 also includes at least one tray 2624 for receiving liquids that might drip from the cover of the sampling tube 220.

The plurality of columns 2621 are arranged corresponding to the arrangement of the sampling tubes 220, so that the cover opening and closing operations for a plurality of sampling tubes can be performed at the same time. In addition, with this kind of screwing-type cover opening and closing module 262, the space required for completing the cover opening and closing operations is limited to the space above the sampling tubes without requiring other extra space. Therefore, the sampling tubes 220 can have a compact arrangement to maximize the amount in batch, which is helpful for speeding up the processing of samples.

The clamping-type cover opening and closing module 263 is aimed at the kind of sampling tube with a cover having thread structures at only one side. The clamping-type cover opening and closing module 263 includes clamping claws 2631 capable of moving in the Z-axis direction to open and close the cover by means of clamping and grabbing. The clamping claws 2631 also can be rotated in 360 degrees for adjusting the angles of clamping and grabbing in response to different types of covers.

The visual identification module 264 is used to capture the image inside the first operation area 20 so as to identify various objects within the space and also the information bearing on the objects, such as to identify the shape, the color, the 1D/2D barcode on the object, the position of the object etc., so as to ensure correct arrangements of the objects on each carrying board and a smooth movement and operation of each module in the operation module assembly 26. In an embodiment, the visual identification module 264 includes a camera and a light source for capturing a clear image, and the image is analyzed and calculated through algorithms for obtaining the required information. Further, the visual identification module 264 also includes a bracket 2641 for engaging with the base 260.

Under the architecture above, the overall operation process of the apparatus 1 is as follows. Firstly, the door 11 is opened. The extraction plate carrying board 24a is moved to a position close to the door 11 for placing the nucleic acid extraction plates 241 thereon and then moved away from the door 11 and into the extraction region 31 of the second operation area 30. The pipette tip carrying board 23 is also moved to a position close to the door 11 for placing the tip racks 2301a, 2301b and the collection plate 231 and then moved away from the door 11 to a position close to the separation wall 50. The sampling tube carrying board 22 and the extraction plate carrying board 24b are moved to positions close to the door 11 for respectively placing the nucleic acid extraction plates 241 on the extraction plate carrying board 24b and placing the row-type tube rack 2201 and/or the tray-type tube rack 2202, the reagent tube rack 225 and the nucleic acid assay plate 224 on the sampling tube carrying board 22. At this time, if the row-type tube rack 2201 is placed, the lateral barcode scanner scans the barcodes simultaneously. After all the placements are completed, the door 11 is closed.

Then, the visual identification module 264 captures the image inside the first operation area 20 for confirming the positions, the amounts and/or the barcodes of all objects. At this time, if the tray-type tube rack 2202 is placed, the bottom barcode scanner 25a scans the barcodes simultaneously. Further, the pipettor module 261 checks if the amounts of the reagents are sufficient through detecting liquid surfaces of the reagents to calculate and estimate liquid volumes. If the amounts of the reagents are insufficient, the pipettor module 261 sends out an alarm for notifying the operator to supply the reagents.

After completing the checking, the operation starts. Within the first operation area 20, the liquids in the sampling tubes on the sampling tube carrying board 22 are transferred to the nucleic acid extraction plates 241 on the extraction plate carrying board 24a and/or 24b. Then, the nucleic acid extraction plates 241 are moved into the extraction region 31 and/or 32 along with the extraction plate carrying board 24a and/or 24b for performing the nucleic acid extraction in the second operation area 30, and at the same time, within the first operation area 20, the preparation of reagents is also performed. Afterwards, the extracted nucleic acids in the nucleic acid extraction plates 241 are transferred to the nucleic acid assay plate 224 on the sampling tube carrying board 22. At this point, the automated operation is completed, and the door 11 is opened, so that the operator can take out the nucleic acid assay plate 224 for subsequent nucleic acid analysis.

From closing the door 11 to initiate the automated operation until opening the door 11, the air circulation systems of the first operation area 20 and the second operation area 30 are continuously under operation for maintaining the flows in single and low-to-high directions. After the automated operation is completed and all objects on the carrying boards are taken out by the operator to clear the interior of the apparatus 1, the door 11 is closed again, and the ultraviolet lamps and the air circulation systems are turned on to clean the internal space of the apparatus 1 for next use.

In conclusion, the nucleic acid processing apparatus 1 of the present disclosure employs the separation wall 50 to separate the first operation area 20 from the second operation area 30, so that the processing procedures in the two operation areas can be performed simultaneously without influencing each other. Further, through the designs that the carrying boards are classified by functions of objects placed thereon and each carrying board is able to move in the X-axis direction independently, cooperating with the operation module assembly 26 is able to move in the Y-axis direction and each module is able to move in the Z-axis direction simultaneously, the time required for processing the nucleic acids before the nucleic acid analysis is effectively reduced to improve the performance, and also, the internal space of the nucleic acid processing apparatus 1 is utilized more effectively to minimize the whole volume thereof.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An integrated nucleic acid processing apparatus, comprising:
    a first operation area, comprising
    a sampling tube carrying board for placing a plurality of sampling tubes;
    a pipette tip carrying board for placing at least one tip rack with a plurality of pipette tips accommodated therein;
    two extraction plate carrying boards, wherein each of the extraction plate carrying boards are configured to carry a plurality of nucleic acid extraction plates and each of the nucleic acid extraction plates has a plurality of magnetic rod sleeves disposed therein;
    a barcode scanner for scanning a plurality of barcodes on the plurality of sampling tubes;
    a pipettor module configured to combine the pipette tips so as to transfer samples in the plurality of sampling tubes to at least one of the plurality of nucleic acid extraction plates;
    a cover opening and closing module for opening and closing a plurality of covers of the plurality of sampling tubes; and
    a visual identification module comprising a camera for capturing an image inside the first operation area,
    wherein the sampling tube carrying board, the pipette tip carrying board and the two extraction plate carrying boards are respectively mounted on a rail for moving in an X-axis direction,
    wherein the pipettor module and the visual identification module are configured to move in a Y-axis direction and a Z-axis direction;
    a second operation area comprising two extraction regions arranged in upper and lower positions, each of the two extraction regions comprising: a magnetic rod holder for mounting thereon a plurality of magnetic rods; and
    a magnetic rod sleeve connector holder for mounting thereon a plurality of magnetic rod sleeve connectors configured to connect with the plurality of magnetic rod sleeves disposed in the plurality of nucleic acid extraction plates; and
    a separation wall for separating the first operation area from the second operation area and having two door sheets spatially corresponding to the two extraction regions,
    wherein the two extraction plate carrying boards are spatially corresponding to the two door sheets and arranged in upper and lower positions, the two extraction plate carrying boards configured to move from the first operation area to the second operation area as the two door sheets are opened, such that a plurality of nucleic acid extraction operations are configured to be performed and isolated using the plurality of magnetic rods, the plurality of magnetic rod sleeve connectors and the plurality of magnetic rod sleeves in the second operation area as the two door sheets are closed.

2. The integrated nucleic acid processing apparatus as claimed in claim 1, wherein the lower extraction plate carrying board and the sampling tube carrying board are located on a first plane and are selectively moved together through a mechanic connection therebetween.

3. The integrated nucleic acid processing apparatus as claimed in claim 2, wherein the pipette tip carrying board is located on a second plane which is higher than the first plane, and the upper extraction plate carrying board is located on a third plane which is higher than the second plane.

4. The integrated nucleic acid processing apparatus as claimed in claim 1, further comprising a housing for enclosing an independent space inside the integrated nucleic acid processing apparatus, and the housing comprises a door capable of being opened.

5. The integrated nucleic acid processing apparatus as claimed in claim 4, wherein the door, the first operation area and the second operation area are sequentially arranged in the X-axis direction.

6. The integrated nucleic acid processing apparatus as claimed in claim 1, wherein the first operation area and the second operation area respectively comprises an independent air circulation system, and each of the air circulation systems provides an airflow moved in a low-to-high direction.

7. The integrated nucleic acid processing apparatus as claimed in claim 1, further comprising high efficiency particulate air filters for respectively filtering air flowed in and out of the first operation area and the second operation area.

8. The integrated nucleic acid processing apparatus as claimed in claim 1, wherein the sampling tube carrying board comprises a plurality of hollow outs corresponding to the plurality of sampling tubes, and the barcode scanner comprises a bottom barcode scanner for scanning the plurality of barcodes on bottom portions of the plurality of sampling tubes.

9. The integrated nucleic acid processing apparatus as claimed in claim 1, wherein the barcode scanner comprises a lateral barcode scanner for scanning the plurality of barcodes on side walls of the plurality of sampling tubes.

10. The integrated nucleic acid processing apparatus as claimed in claim 1, wherein the sampling tube carrying board comprises a first placing region and a second placing region for respectively carrying different types of sampling tubes.

11. The integrated nucleic acid processing apparatus as claimed in claim 1, wherein the sampling tube carrying board further has a nucleic acid assay plate disposed thereon for accommodating extracted nucleic acids after the plurality of nucleic acid extraction operations.

12. The integrated nucleic acid processing apparatus as claimed in claim 1, wherein the sampling tube carrying board further has a reagent tube rack disposed thereon for accommodating a plurality of reagent tubes, and a cooling module is disposed at a position corresponding to the reagent tube rack.

13. The integrated nucleic acid processing apparatus as claimed in claim 1, wherein the plurality of pipette tips are re-positioned in the at least one tip rack after being used.

14. The integrated nucleic acid processing apparatus as claimed in claim 1, wherein the pipette tip carrying board further has a collection plate disposed thereon for serving as a nucleic acid assay plate or a sample reserving plate.

15. The integrated nucleic acid processing apparatus as claimed in claim 1, wherein each of the extraction plate carrying boards comprises a heating module for providing temperature variations during the plurality of nucleic acid extraction operations.

16. The integrated nucleic acid processing apparatus as claimed in claim 1, wherein the cover opening and closing module comprises a screwing-type cover opening and closing module and a clamping-type cover opening and closing module.

17. The integrated nucleic acid processing apparatus as claimed in claim 1, further comprising a plurality of trays disposed under the pipettor module and the cover opening and closing module.

18. The integrated nucleic acid processing apparatus as claimed in claim 1, further comprising ultraviolet lamps respectively disposed in the first operation area and the second operation area for cleaning and sterilization.

19. The integrated nucleic acid processing apparatus as claimed in claim 1, further comprising a controller and at least one motor for respectively controlling and driving the sampling tube carrying board, the pipette tip carrying board, the two extraction plate carrying boards, the barcode scanner, the pipettor module, the cover opening and closing module, the visual identification module, the magnetic rod holder, the magnetic rod sleeve connector holder and the two door sheets.

* * * * *